(12) United States Patent
Sebree et al.

(10) Patent No.: US 8,475,830 B2
(45) Date of Patent: Jul. 2, 2013

(54) IMPLANTS FOR THE TREATMENT OF DOPAMINE ASSOCIATED STATES

(75) Inventors: Terri B. Sebree, Gladwyne, PA (US); Steven J. Siegel, Berwyn, PA (US)

(73) Assignees: NuPathe Inc., Conshohocken, PA (US); The Trustees of the University of Pennsylvania, Philadelphia, PA (US)

( * ) Notice: Subject to any disclaimer, the term of this patent is extended or adjusted under 35 U.S.C. 154(b) by 592 days.

(21) Appl. No.: 12/074,101

(22) Filed: Feb. 29, 2008

(65) Prior Publication Data
US 2008/0152693 A1 Jun. 26, 2008

Related U.S. Application Data

(62) Division of application No. 11/784,526, filed on Apr. 6, 2007.

(60) Provisional application No. 60/789,961, filed on Apr. 6, 2006.

(51) Int. Cl.
*A61F 2/02* (2006.01)

(52) U.S. Cl.
USPC ........... 424/426; 424/422; 424/423; 424/424; 514/415

(58) Field of Classification Search
USPC ................... 424/422, 423, 424, 426; 514/415
See application file for complete search history.

(56) References Cited

U.S. PATENT DOCUMENTS

| 4,452,808 | A | | 6/1984 | Gallagher, Jr. | |
|---|---|---|---|---|---|
| 4,666,704 | A | * | 5/1987 | Shalati et al. | 424/424 |
| 4,824,860 | A | | 4/1989 | Owen et al. | |
| 4,883,666 | A | * | 11/1989 | Sabel et al. | 424/422 |
| 4,912,126 | A | | 3/1990 | Owen et al. | |
| 5,021,335 | A | * | 6/1991 | Tecott et al. | 435/6 |
| 6,319,512 | B1 | | 11/2001 | Rothen-Weinhold et al. | |
| 2001/0029262 | A1 | | 10/2001 | Sethi | |
| 2001/0034345 | A1 | | 10/2001 | Greenamyre et al. | |
| 2001/0056115 | A1 | | 12/2001 | Tulloch | |
| 2002/0103250 | A1 | | 8/2002 | Sethi | |
| 2002/0179096 | A1 | * | 12/2002 | Siegel et al. | 128/898 |
| 2003/0060499 | A1 | | 3/2003 | Tulloch | |
| 2003/0153612 | A1 | | 8/2003 | Sethi | |
| 2004/0157910 | A1 | | 8/2004 | Sethi | |
| 2005/0031667 | A1 | * | 2/2005 | Patel et al. | 424/426 |
| 2007/0224247 | A1 | * | 9/2007 | Chudzik et al. | 424/427 |

FOREIGN PATENT DOCUMENTS

| CA | 1333770 | 1/1995 |
|---|---|---|
| JP | A-H01-216917 | 8/1989 |
| WO | WO 97/11696 A | 4/1997 |
| WO | WO 02/15903 A2 | 2/2002 |
| WO | WO-2005/070332 A1 | 8/2005 |
| WO | WO 2005/107727 A1 | 11/2005 |

OTHER PUBLICATIONS

International Search Report for Application No. PCT/US05/00884, dated Mar. 28, 2005.
International Search Report for Application No. PCT/US07/08740, dated Feb. 28, 2008.
Lu bin et al., Pharmaceutics, China Medical Science Press, Textbook for pharmaceutical majors in Higher Medical Colleges and Universities ISBN 7-5067-2677-7, Jan. 2003, p. 428.

* cited by examiner

*Primary Examiner* — Ali Soroush
(74) *Attorney, Agent, or Firm* — McCarter & English, LLP; Danielle L. Herritt, Esq.; A. Jacqueline Wizeman

(57) ABSTRACT

Biodegradable implants comprising dopamine modulating compounds are described.

16 Claims, 2 Drawing Sheets

IMPLANTS FOR THE TREATMENT OF DOPAMINE ASSOCIATED STATES

RELATED APPLICATIONS

This application is a divisional of U.S. patent application Ser. No. 11/784,526, filed on Apr. 6, 2007; which claims priority to U.S. Provisional Application Ser. No. 60/789,961, filed on Apr. 6, 2006. The entire contents of each of the aforementioned applications are hereby incorporated herein by reference.

BACKGROUND OF THE INVENTION

Parkinson's disease is a progressive degenerative disease of the central nervous system. The risk of developing Parkinson's disease increases with age, and afflicted individuals are usually adults over 40. Parkinson's disease occurs in all parts of the world, and affects more than one million individuals in the United States alone.

While the primary cause of Parkinson's disease is not known, it is characterized by degeneration of dopaminergic neurons of the substantia nigra. The substantia nigra is a portion of the lower brain, or brain stem, that helps control voluntary movements. The shortage of dopamine in the brain caused by the loss of these neurons is believed to cause the observable disease symptoms.

The symptoms of Parkinson's disease vary from patient to patient. The most common symptom is a paucity of movement, e.g., rigidity characterized by an increased stiffness of voluntary skeletal muscles. Additional symptoms include resting tremor, bradykinesia (slowness of movement), poor balance, and walking problems. Common secondary symptoms include depression, sleep disturbance, dizziness, stooped posture, dementia, and problems with speech, breathing, and swallowing. The symptoms become progressively worse and ultimately result in death.

Surgical treatments available for Parkinson's disease include pallidotomy, brain tissue transplants, and deep brain stimulation. Such treatments are obviously highly invasive procedures accompanied by the usual risks of brain surgery, including stroke, partial vision loss, speech and swallowing difficulties, and confusion.

A variety of chemotherapeutic treatments for Parkinson's disease are also available. Perhaps the best known is administration of levodopa, a dopamine precursor. While levodopa administration can result in a dramatic improvement in symptoms, patients can experience serious side-effects, including nausea and vomiting. Concurrent carbidopa administration with levodopa is a significant improvement, with the addition of carbidopa inhibiting levodopa metabolism in the gut, liver and other tissues, thereby allowing more levodopa to reach the brain. Additional therapeutic approaches include the use of dopamine agonists such as ropinirole, pergolide and apomorphine.

SUMMARY OF THE INVENTION

The invention pertains, at least in part, to a method for treating a subject for a dopamine associated state. The method includes administering to a subject a biodegradable implant. The implant comprises an effective amount of a dopamine modulating compound for the treatment of a dopamine associated state.

In another embodiment, the invention includes a biodegradable implant, which includes a dopamine modulating compound and a biodegradable polymer.

In yet another embodiment, the invention also pertains, at least in part, to a method for maintaining a therapeutic plasma level of a dopamine modulating compound in a subject. The method includes administering to the subject an implant comprising a biodegradable polymer and the dopamine modulating compound, such that the plasma level of the compound is maintained for at least one day.

In a further embodiment, the invention also pertains at least in part, to a method for treating a subject for Parkinson's disease. The method includes administering to a subject a biodegradable implant, wherein the implant comprises an effective amount of ropinirole to treat Parkinson's disease.

In another further embodiment, the invention also includes a biodegradable implant, comprising ropinirole and a biodegradable polymer.

DETAILED DESCRIPTION OF THE INVENTION

Figure 1:
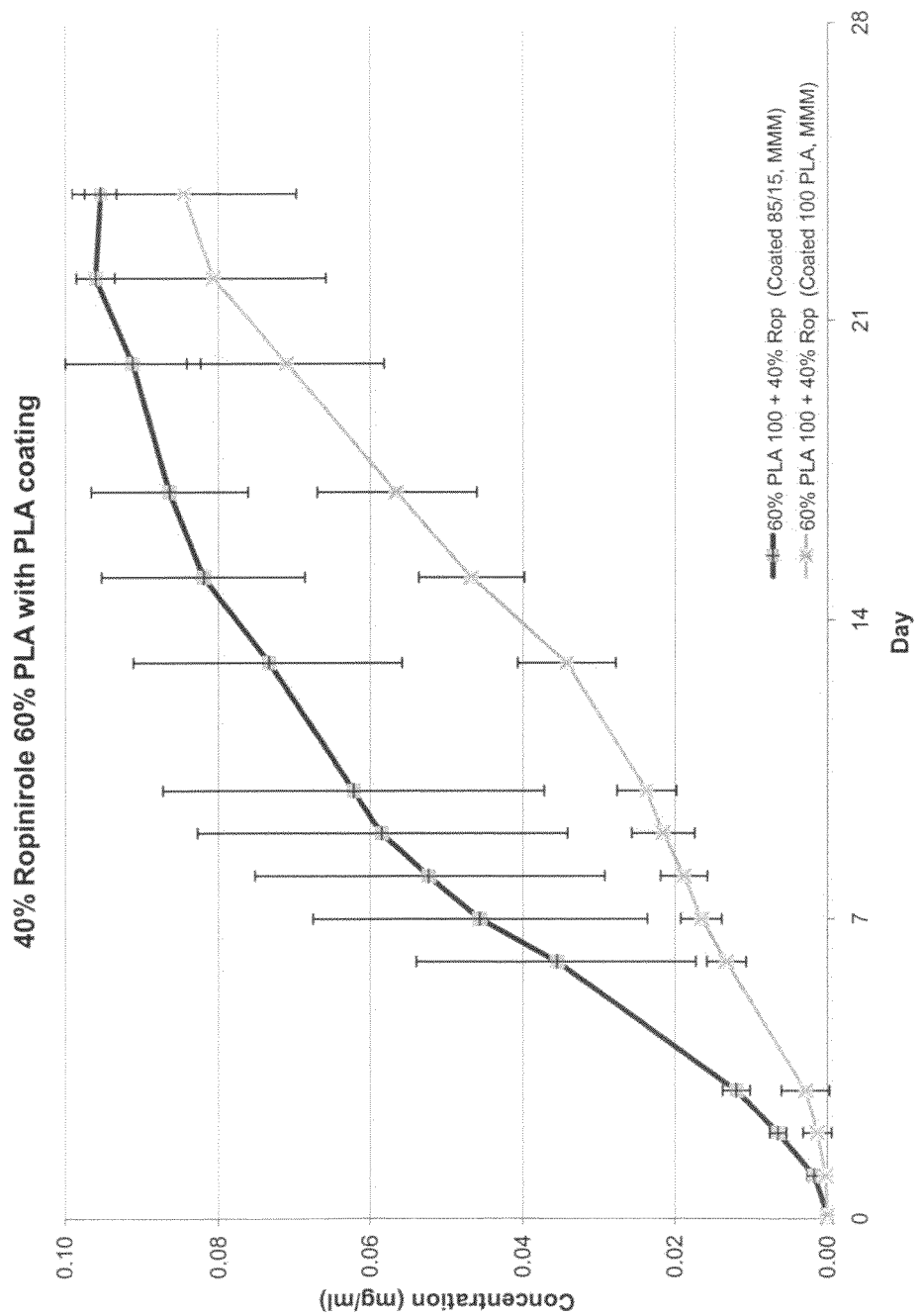
FIG. 1 is a graph which shows the release patterns of 40% ropinirole/60% PLA implant with coatings of 85:15 PLGA (+) and 100 PLA (X).

In one embodiment, the invention pertains to a method for treating a subject for a dopamine associated state. The method includes administering to the subject a biodegradable implant, which comprises an effective amount of a dopamine modulating compound.

The term "dopamine associated state" includes states which can be treated by the administration of a dopamine modulating compound or otherwise associated with the presence or absence of dopamine. Examples of dopamine associated states include Parkinson's disease, attention deficit disorder (ADD), attention deficit hyperactivity disorder (ADHD), autism, pervasive development disorder (PDD), Asberger's syndrome, toxin-induced parkinsonism, disease-induced parkinsonism, erectile dysfunction, restless leg syndrome, and hyperprolactinemia. The term "Parkinsonism" includes conditions resulting from injury to the central nervous system that may cause an individual to exhibit symptoms similar to those of Parkinson's disease. Parkinsonism may result, for example, from toxin exposure, for example, carbon monoxide or manganese poisoning or MPTP administration, or from a disease condition such as encephalitis.

The term "dopamine modulating compound" includes both dopamine agonists and antagonists. In a further embodiment, the dopamine modulating compound is a dopamine agonist. Examples of dopamine agonists include compounds which are capable of binding to one or more dopamine receptor subgroups, resulting in beneficial therapeutic effect in an individual treated with the agonist. The dopamine agonists may be agonists for at least the D2 subgroup of dopamine receptors, and also may be agonists for D1 and/or D3 receptors. Examples of dopamine modulating compounds of the invention include apomorphine, lisuride, pergolide, bromocriptine, pramipexole, 4-alkylamino-2(3H)-indolone compounds (e.g., ropinirole), rotigotine, docarpamine, terguride, cabergoline, levodopa, spheramine, romergoline, carmoxirole, zelandopam, sumanirole, sibenadet, and combinations of two or more of these dopamine agonists. Pharmaceutically acceptable salts, esters, prodrugs, and metabolites of these compounds are also included. In one further embodiment, the dopamine agonist compound is ropinirole.

The term "4-alkylamino-2(3H)-indolone compound" includes compounds of the formula (I):

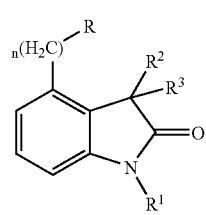

wherein:

R is amino, alkylamino, di-alkylamino, alkenylamino, dialkenylamino, N-alkyl-N-alkenylamino, benzylamino, dibenzylamino, arylalkylamino, or diarylalkylamino;

$R^1$, $R^2$ and $R^3$ are each independently hydrogen or alkyl; and n is 1, 2, or 3, and pharmaceutically acceptable salts thereof.

In a further embodiment, R is 4-hydroxyphenethylamino or di-(4-hydroxyphenethylamino). In another further embodiment, R is amino, di-n-propylamino, n-propyl-n-butylamino or 4-hydroxyphenethylamino. In an embodiment, $R^1$, $R^2$, and $R^3$ are each lower alkyl (e.g., 1-6 carbons). In another further embodiment, $R^1$, $R^2$, and $R^3$ are each hydrogen. In yet another further embodiment, n is 2. In one embodiment, the compound of formula (I) is 4-(2-di-n-propylaminoethyl)-2(3H)-indolone ("ropinirole") or a pharmaceutically acceptable salt thereof.

The term "lower alkyl" includes branched and straight chain groups of from 1-6 carbons, preferably methyl, ethyl, propyl, or butyl for each alkyl in R and from 1-4 carbons, preferably methyl, for each of $R^1$, $R^2$ and $R^3$.

Pharmaceutically acceptable acid addition salts of the dopamine modulating compounds are also part of this invention. The salts are prepared by methods well known to the art and are formed with both inorganic or organic acids, for example: maleic, fumaric, benzoic, ascorbic, pamoic, succinic, bismethylenesalicylic, methane sulfonic, ethane disulfonic, acetic, oxalic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids. The hydrohalic salts may be conveniently used.

The alkylated products may be prepared by alkylation of the parent amino compounds of formula I in which R is amino or a secondary amino. For example, the N-alkylated products, formula I when R is a secondary or tertiary amino, are conveniently prepared by reductive alkylation using, for example, the aldehyde in one or two molar equivalent quantities under reduction conditions, such as under catalytic hydrogenation conditions over a palladium or platinum catalyst or such as using formaldehyde-formic acid when R is dimethylamino.

N-Alkylation, such as using an allyl or benzyl halide in the presence of an acid binding agent, can be used under standard mild conditions. Protecting the amido hydrogen in the ring is also used during alkylation if necessary as known to the art. Alkyl substituents at the 1 or 3-positions of the indolone ring are introduced by forming the lithio derivatives at the ring position, such as using butyl lithium, followed by reaction with a lower alkyl halide, especially an alkyl iodide.

The term "implant" includes surgically implantable devices comprised of one or more sections. The sections may be of any size which allows the implant to perform its intended function. In one embodiment, the sections and/or implant are removable from the subject. In another embodiment, the implant is comprised of 1, 2, 3, 4, 5, 6, 7, 8, 9, 10, or more discrete sections. In another embodiment, the section may be rod shaped. In a further embodiment, the implant is comprised of a biocompatible and/or biodegradable polymer. Preferably, the implants are removable through out the time period when the dopamine modulating compound is being released to the subject at therapeutic levels. The sections may be shaped as rods, disks, crescents, cones, spheres or any other shape which allows for the implant to perform its intended function. In one embodiment, the sections are macroscopic (e.g., at least 1 mm in diameter). In a further embodiment, the sections are rod shaped. In another further embodiment, the diameter of the sections are about 0.5 to about 5 mm in diameter and about 0.5 cm to about 10 cm in length. In another further embodiment, the diameter of the sections are about 0.5 to about 5 mm in diameter and about 0.5 cm to about 5 cm in length. In another further embodiment, the sections are about 1 mm to about 3 mm in diameter and about 1 cm to about 3 cm in length.

In certain embodiments, the term "implant" also includes microparticles. The microparticles are particles of a spherical shape, although sometimes the microparticles may be irregularly shaped. The microparticles can vary in size, ranging from submicron to 1 mm or less. In a further embodiment, the microparticles are 1-500 microns, more preferably, 25-180 microns, and are prepared such that administration of the microparticles to a subject can be carried out with a standard gauge needle.

The microparticles may be administered to a subject in a single administration, releasing the drug in a constant or pulsed manner into the subject and eliminating the need for repetitive injections. The microparticles can be mixed by size or by type so as to provide for the delivery of the dopamine modulating compound to the subject in a multiphasic manner and/or in a manner that provides different agents to the subject at different times, or a mixture of agents at the same time.

The microparticles can be prepared by any method capable of producing microparticles. One method of preparation is that described in U.S. Pat. No. 4,389,330. In this method the compound is dissolved or dispersed in an appropriate solvent. The polymeric matrix material is added to the compound containing medium in an amount relative to its desired loading. Optionally, all of the ingredients of the microparticle product can be blended in the solvent medium together.

Solvents for the compound and the polymeric matrix material that can be employed include organic solvents, such as acetone; halogenated hydrocarbons, such as chloroform, methylene chloride, and the like; aromatic hydrocarbon compounds, halogenated aromatic hydrocarbon compounds; cyclic ethers; alcohols, such as, benzyl alcohol; ethyl acetate; and the like.

The term "biodegradable" includes implants which comprise polymers which degrade by bodily processes to products readily disposable by the body and, advantageously, do not accumulate in the body. The products of the biodegradation should also be biocompatible with the body in the same sense that the polymeric matrix is biocompatible with the body. Suitable examples of biodegradable polymers include poly(glycolic acid), poly-D,L-lactic acid, poly-L-lactic acid (PLA), copolymers of the foregoing (e.g., PLGA, e.g., 85:15

PLGA, 75:25 PLGA, 50:50 PLGA, etc.), poly(aliphatic carboxylic acids), copolyoxalates, polycaprolactone (PCL), polydioxonone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. Furthermore, some polymers may also be modified with end cap modifications such as alkyl caps. Such end caps are described in *Journal of Controlled Release* 52 (1998) 53-62 and *Journal of Controlled Release* 67 (2000) 281-292, the contents of each of which are incorporated herein by reference.

In a further embodiment, the polymer is selected so that it interacts with the dopamine modulating compound via ionic interactions. These interactions may retard the release of a charged or ionically active dopamine modulating compound. For example, a positively charged dopamine modulating compound such as ropinirole HCl may interact with a negatively charged polymer.

In one embodiment, the implant is comprised of a polymer that is biocompatible. The term "biocompatible" includes polymers which are not toxic to the human body, are not carcinogenic, and do not significantly induce inflammation in body tissues.

In one embodiment, the polymer comprises polylactide or a copolymer comprising polylactide such as dl(polylactide-co-glycolide). Examples of such biodegradable polymers include those which comprise about 30 to 100% polylactide and 0 to 70% polyglycolide. The copolymer and the dopamine modulating compound may be fabricated into an implant via solvent casting and compression molding. In an embodiment, the individual polymers and the compound are dissolved in an organic solvent and solvent cast at a temperature at which the solvent evaporates for a period of time which allows for complete drying of the polymer-compound mixture. Complete drying can be assessed by weighing the material at the beginning of solvent casting and at the end of the solvent casting to ensure that all solvent has been evaporated. It may be noted that care should be taken to form a homogenous mixture to avoid the creation of macroscopic areas of high concentrations of the dopamine modulating compound which may result in "drug dumping."

In a further embodiment, the implants of the invention may further comprise a hydrophobic coating which may comprise one or more hydrophobic polymers. Examples of such hydrophobic polymers include PLGA (including but not limited to 85:15 PLGA, 75:25 PLGA, 50:50 PLGA, etc.), polycapralactone (PCL), PLA, ethylcellulose, and combinations and co-polymers thereof (including, but not limited to, PLGA-co-PCL and PLA-co-PCL). In a further embodiment, the hydrophobic polymers are selected to reduce water permeability of the implant and slow the release of the dopamine modulating compound. The hydrophobic coating may be applied to the implant by dip coating the implant in a solution of the polymer (e.g., a 10% PLA solution). In another further embodiment, the hydrophobic coating is selected such that the drug is delivered gradually rather than with an initial burst (e.g., the amount of drug administered within the first day or week is significantly more (e.g., about 50% more, about 75% or more, about 100% or more, about 200% or more or about 500% or more) than the rate of release of the drug two or three weeks after implantation.

The dopamine modulating compound concentrations may range from about 5% to about 95%, from about 10% to about 80%, from about 20% to about 60%, or from about 30% to about 50% in the implant depending upon the release period.

In a further embodiment, the dopamine modulating compound concentration is about 20% or about 40%.

In a further embodiment, the implant releases about 0.05%, about 0.1%, about 0.5%, about 1%, about 1.5%, about 2%, about 3%, about 3.5%, about 4%, about 4.5%, about 5%, about 5.5%, about 6%, about 7%, about 7.5%, about 8%, about 8.5%, about 9%, about 9.5% or about 10% of the dopamine modulating compound in the implant per day.

The term "subject" includes animals (e.g., mammals, e.g., cats, dogs, horses, pigs, cows, sheep, rodents, rabbits, squirrels, bears, primates (e.g., chimpanzees, gorillas, and humans)) which are capable of (or currently) suffering from dopamine associated states. It also includes transgenic animal models. In a further embodiment, the subject is a human suffering from Parkinson's disease or disease or toxin induced parkinsonisms.

The term "treated," "treating" or "treatment" includes therapeutic and/or prophylactic treatment of a dopamine associated state. The treatment includes the diminishment or alleviation of at least one symptom associated or caused by the dopamine associated state. For example, treatment can be diminishment of one or several symptoms of the dopamine associated state or complete eradication.

The language "effective amount" of the dopamine modulating compound is that amount necessary or sufficient to treat or prevent a dopamine associated state in a subject, e.g. prevent the various morphological and somatic symptoms of a dopamine associated state in a subject. The effective amount can vary depending on such factors as the size and weight of the subject, the type of illness, or the particular dopamine modulating compound. For example, the choice of the dopamine modulating compound can affect what constitutes an "effective amount".

The term "effective amount" also includes the amount of the dopamine modulating compound that will render a desired therapeutic outcome, e.g., a level or amount effective to reduce symptoms of a dopamine associated state such as Parkinson's disease and/or increase periods of therapeutic effectiveness ("on" periods) for a patient undergoing chronic dopaminergic therapy for idiopathic Parkinson's disease or toxin- or disease-induced parkinsonism, or beneficial treatment, i.e., reduction or alleviation of adverse or undesirable symptoms of a condition treatable with a dopamine agonist, such as erectile dysfunction, restless leg syndrome, or hyperprolactinemia. For treatment of Parkinson's disease or parkinsonism, effectiveness is often associated with reduction in "on"/"off" fluctuations associated with a particular Parkinson's disease treatment regime, such as for example, chronic levodopa administration. An amount that is "therapeutically effective" for a particular subject may depend upon such factors as a subject's age, weight, physiology, and/or the particular symptoms or condition to be treated, and will be ascertainable by a medical professional.

In a further embodiment, the effective amount of the dopamine modulating compound is the amount necessary to achieve a plasma concentration of the dopamine modulating compound of about 0.5 to about 100 ng/mL, of about 0.5 to about 90 ng/mL, of about 0.5 to about 80 ng/mL, of about 0.5 to about 70 ng/mL, of about 0.5 to about 60 ng/mL, of about 0.5 to about 50 ng/mL, 1 ng/ml to about 40 ng/ml, about 1 ng/ml to about-30 ng/ml, about 1 ng/ml to about 20 ng/ml, 1 ng/ml to about 15 ng/ml, or about 2.5 ng/ml to about 10 ng/ml. In a further embodiment, the effective amount is effective to maintain the aforementioned plasma concentration for at least one day or longer, one week or longer, two weeks or longer, three weeks or longer, four weeks or longer, six weeks or longer, two months or longer, three months or longer, four months or longer, five months or longer, six months or longer, seven months or longer, eight months or longer, nine months or longer, ten months or longer, eleven months or longer, twelve months or longer, or over a year or longer.

The term "administering" include surgically administering, implanting, inserting, or injecting the implant (or sections thereof) into a subject. The implant (or section) can be located subcutaneously intramuscularly, or located at another body location which allow the implant to perform its intended function. Generally, implants (or sections) are administered by subcutaneous implantation at sites including, but not limited to, the upper arm, back, or abdomen of a subject. Other suitable sites for administration may be readily determined by a medical professional. Multiple implants or sections may be administered to achieve a desired dosage for treatment.

In another embodiment, the invention pertains to a biodegradable implant, comprising a dopamine modulating compound and a biodegradable polymer. In a further embodiment, the implant comprises an effective amount of a dopamine modulating compound to treat a dopamine associated state, such as Parkinson's disease.

In a further embodiment, the dopamine modulating compound is present in an amount in the implant which is effective to maintain an effective plasma level of the compound. In a further embodiment, the effective plasma level is at least 1 ng/ml for at least one day, one week, one month, two months, three months, four months, five months, six months, seven months, eight months, nine months, ten months, eleven months or twelve months or longer. In a further embodiment the plasma level of the dopamine modulating compound is between about 1 ng/ml and about 100 ng/ml, about 1 ng/ml and about 90 ng/ml, about 1 ng/ml and about 80 ng/ml, about 1 ng/ml and about 70 ng/ml, about 1 ng/ml and about 60 ng/ml, about 1 ng/ml and about 50 ng/ml, about 1 ng/ml and about 40 ng/ml, about 1 ng/ml and about 30 ng/ml, about 1 ng/ml and about 20 ng/ml, or about 1 ng/ml and about 10 ng/ml.

In another embodiment, the invention also includes a method for maintaining an effective plasma level of a dopamine modulating compound in a subject. The method includes administering to the subject an implant comprising a biodegradable polymer and a dopamine modulating compound, such that the plasma level of said compound is maintained for at least one day. In a further embodiment, the effective amount is between about 1 ng/ml and about 100 ng/ml, about 1 ng/ml and about 90 ng/ml, about 1 ng/ml and about 80 ng/ml, about 1 ng/ml and about 70 ng/ml, about 1 ng/ml and about 60 ng/ml, 1 ng/ml and about 50 ng/ml, about 1 ng/ml and about 40 ng/ml, about 1 ng/ml and about 30 ng/ml, about 1 ng/ml and about 20 ng/ml, or about 1 ng/ml and about 10 ng/ml. In another embodiment, the plasma levels are maintained for at least one day, one week, one month, two months, three months, four months, five months, six months, seven months, eight months, nine months, ten months, eleven months or twelve months or longer.

The invention also pertains to methods comprising administering second agents in combination with the biodegradable implants of the invention. The second agents may be any agent which enhances or increases the effectiveness of the treatment of the dopamine associated state and/or reduce inflammation at the site of administration of the biodegradable implant, or which prevents or retards oxidation of the dopamine modulating compounds. For example, an anti-inflammatory agent, such as for example, a steroid (e.g., dexamethasone, triamcinolone, betamethasone, clobetasol, cortisone, hydrocortisone, or a pharmaceutically acceptable salt thereof), or a nonsteroidal anti-inflammatory agent ("NSAID"; e.g., diclofenac potassium diclofenac sodium, diclofenac sodium with misoprostol, diflunisal, etodolac, fenoprofen calcium, flurbiprofen, ibuprofen, indomethacin, ketoprofen, meclofenamate sodium, mefenamic acid, meloxicam, nabumetone, naproxen, naproxen sodium, oxaprozin, piroxicam, sulindac, tolmetin, COX-2 inhibitors (e.g., celecoxib, rofecoxib, valdecoxib), acetylated salicylates (e.g., aspirin), nonacetylated salicylates (e.g., choline, magnesium, and sodium salicylates, salicylate)), and/or an antihistamine (e.g., loratadine ("LT"), astemizole, cetrizine dihydrochloride, chlorpheniramine, dexochlorpheniramine, diphenhydramine, mebhydrolin napadisylate, pheniramine maleate, promethazine, or terfenadine). The second agents may be encapsulated within the biodegradable implant to prevent or reduce local inflammation at the site of administration. The second agents may also be administered separately to the subject by any route that allows the second agents to perform their intended functions. The second agents may be administered orally, parentally, topically, subcutaneously, sublingually, etc. Any of the second agents, or a combinations thereof, may also be included in the same implant(s) as dopamine modulating or alternatively, may be incorporated into one or more separate implants or sections thereof that do not include the dopamine modulating compound. An antioxidant, e.g., ascorbic acid, sodium metabisulfite, glutathione, may be included in the same implant or section thereof as dopamine modulating compound to prevent or reduce oxidation of dopamine modulating compound during preparation, storage, and/or administration of the implant or section thereof.

In a further embodiment, the invention also includes a method for treating a subject for Parkinson's disease, comprising administering to the subject a biodegradable implant, wherein the implant comprises an effective amount of ropinirole to treat Parkinson's disease.

In another further embodiment, the invention also pertains to a biodegradable implant, comprising ropinirole and a biodegradable polymer.

The implants (and sections thereof) can be manufactured using methods known in the art. For implants comprised of polymers that are viscose liquids at processing temperatures of 60-80° C. (e.g., polycapralactone and the like), the polymer is melted in an oven, oil bath or by another method known in the art, and the dopamine modulating compound is mixed into the molten polymer with an electric mixer. The homogenous mixture of the dopamine modulating compound and the polymer is then formed into implants by pouring it into molds, and/or by compression molding and/or extrusion.

For implants (or sections thereof) comprised of polymers that require pressure to flow at processing temperature, the dopamine modulating compound and the polymer are melt mixed in a single or twin screw mixer/extruder that heats and kneads the drug and polymer prior to extrusion. The implants (or sections thereof) are then formed by extrusion alone or in combination with compression molding. The implants may further be dip coated with a hydrophobic polymer solution.

Pharmaceutically acceptable acid addition salts of the dopamine modulating compounds are also part of this invention. The salts are prepared by methods well known to the art and are formed with both inorganic or organic acids, for example: maleic, fumaric, benzoic, ascorbic, pamoic, succinic, bismethylenesalicylic, methane sulfonic, ethane disulfonic, acetic, oxalic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids. The hydrohalic salts may be conveniently used.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl(benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxophenyl, quinoline, isoquinoline, naphthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively.

The term "amide" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "hydroxy" or "hydroxyl" includes groups with an —OH or —O$^-$.

The term "halogen" includes fluorine, bromine, chlorine, iodine, etc. The term "perhalogenated" generally refers to a moiety wherein all hydrogens are replaced by halogen atoms.

The term "heteroatom" includes atoms of any element other than carbon or hydrogen. Preferred heteroatoms are nitrogen, oxygen, sulfur and phosphorus.

The term "cyclic" includes saturated or unsaturated, aromatic or non-aromatic ring moieties. Examples of saturated cyclic moieties include piperidine, piperazine, morpholine, cyclohexyl, cyclobutyl, cyclopentyl, etc.

EXEMPLIFICATION OF THE INVENTION

Example 1

Implant Fabrication

Implants are fabricated through solvent casting and compression molding. Four polymers, 100% polylactide (PLA), 85% polylactide with 15% polyglycolide (85:15 PLGA), 65% polylactide with 35% polyglycolide (65:35 PLGA), and 50% polylactide with 50% polyglycolide (50:50 PLGA) are present either alone or in a combined system of release during a 1 to 5-month period. Each copolymer has a distinctive period of degradation, which is determined by the ratio of lactide to glycolide and the molecular weight of the resulting molecule produced. An additional polymer of polycaprolactone (PCL) and or polylactide (PLA) is used for in vivo testing in mice. Individual polymers and ropinirole are dissolved in DMF (dimethyl formamide) or DMSO (dimethyl sulfoxide) and solvent cast while mixing at 150° C. followed by further evaporation for up to 14 days. Solvent cast material are compression molded at 80° and 25,000 psi (density 1.1.±0.10 grams/cc).

Example 2

In Vitro Assay

Individual implants are placed in 0.5 to 1.0 liter of phosphate buffered saline (PBS), pH 7.4 at 37° C. in constant motion. Ropinirole amount are measured by UV spect, HPLC/UV or GCMS. Each assay includes negative controls of implants made of polymer alone and a 100 ng/ml ropinirole standard to assess stability of ropinirole in solution over time. The assay is also repeated using the same procedure at pH 2.0 to 6.4.

Example 3

In Vitro Assay

A 100% PLA implant was evaluated by placing the implant into clean amber glass bottles containing PBS, pH 7.0 at 37° C. on a shaker table. All of the sample implants were designed such that total drug release (approx. 5 or 10 mg depending on load) remained below the solubility limits to create sink conditions (e.g., 10-20 mg/200 ml=0.05-0.10 mg/ml=less than 1% solubility of ropinirole in an aqueous medium). Samples were removed daily (M-F) for three weeks, followed by three times per week thereafter (MWF). All assay sets were run in 96 well plates and included a positive control solution, negative control containing the matched polymer and a blank saline jar. Assays were run with a standard curve at each sample point using the manufacturers UV spectrophotometry quantitation software. Data are graphed for concentration in 200 ml of solution such that 20% implants of exactly 50 mg (10 mg API) would yield a theoretical maximum concentration of 0.05 mg/ml.

FIG. 1 is a graph which shows the release patterns of 40% ropinirole/60% PLA implant with coatings of 85:15 PLGA (+) and 100 PLA (X). It was found that the PLA implants with PLA coatings released approximately 3% of the drug per day.

The corresponds to a delivery interval of approximately 1 month without a distinct burst during the initial period.

Figure 2:
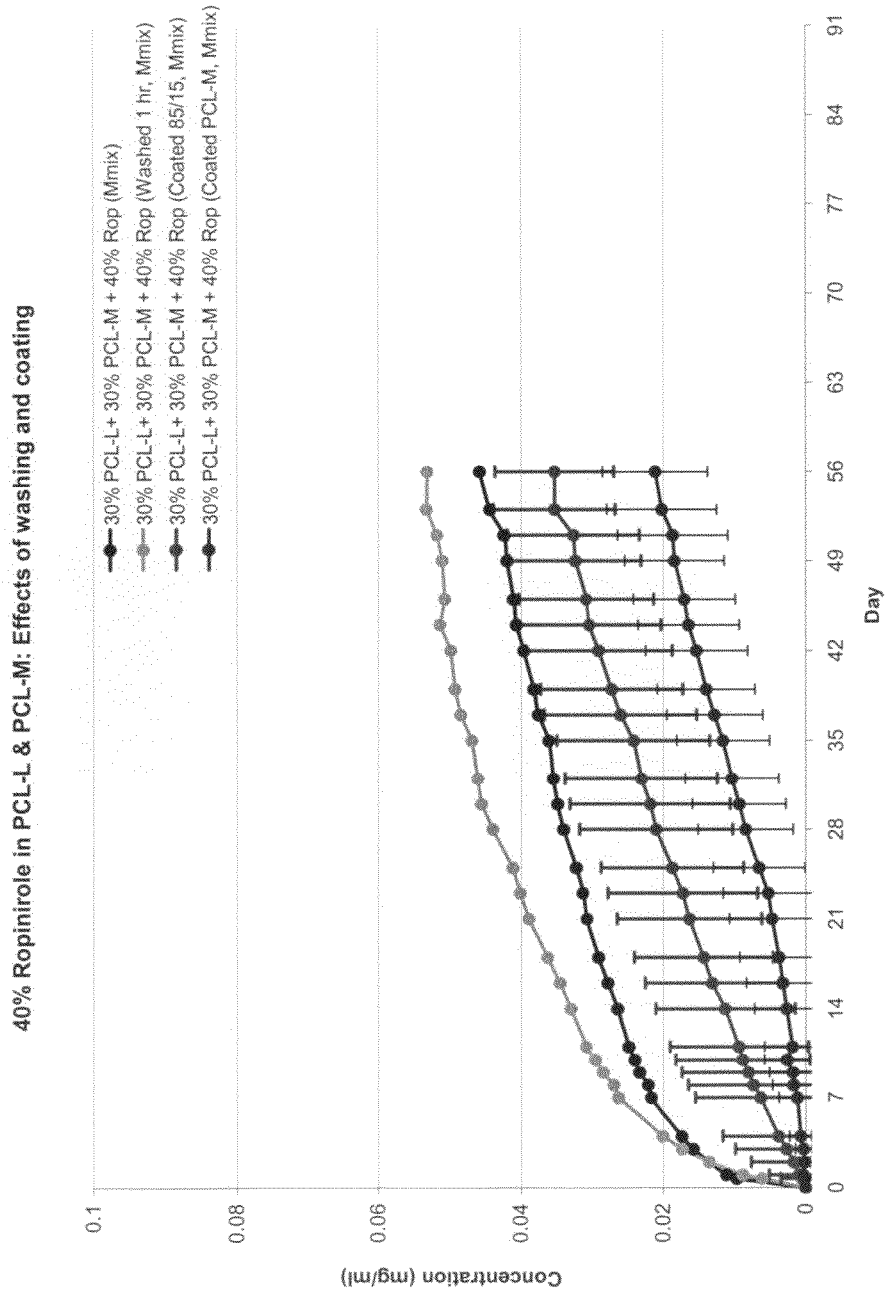
FIG. 2 is a graph which show the release patterns of 40% ropinirole with 30% PCL-L (low molecular weight PCL) and 30% PCL-M (medium moleculular weight PCL).

FIG. 2 is a graph which show the release patterns of 40% ropinirole with 30% PCL-L (low molecular weight PCL) and 30% PCL-M (medium moleculular weight PCL). Also shown in this graph is the effect of either washing to remove surface ropinirole prior to testing or coating with either PCL-M or PGLA. The implants were fabricated using the methods described above and used melt mixing procedures to incorporate 40% drug load with a PCL-M and PCL-L blend.

It was found that both the PLGA and PCL-M coatings effectively retarded the initial burst and produced an implant capable of delivering either 0.3% per day for a 9-10 month preparation (PCL-M coating) or 0.4% per day for a 6 month preparation (PLGA coating).

Example 4

In Vivo Rodent Assay

Implants are also tested in mice (n=16). Animals are maintained with a 12:12 light:dark cycle with all testing and procedures performed during the light cycle.

Mice are anesthetized with isofourane 5% induction 1% maintanance. A 0.1 to 1-cm incision is made in the skin on the dorsal aspect of the animal and an implant is placed between dermis and muscle. Removal of implants is performed with identical anesthesia and incision followed by implant retrieval.

Bioactivity of ropinirole implants are assessed in mice. The mice received implants made of 85:15 PLGA, 65:35 PLGA, 50:50 PLGA or PCL alone or with between 35% and 45% ropinirole to assess the effects of implants on locomotion. Following approximately two, four, six, eight, ten and twelve weeks of implantation, total distance traversed is assessed over a thirty-minute period. Implants are removed at either 6 or 12 weeks and animals sacrificed to assess serum levels.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

The invention claimed is:

1. An implantable device comprising:
   a biodegradable implant, comprising
      a homogenous mixture of at least one biodegradable polymer and a dopamine modulating compound, and
      a biodegradable hydrophobic coating disposed about the homogenous mixture, such that the device delivers dopamine modulating compound gradually rather than with an initial burst and maintains an effective plasma level for at least a desired delivery period;
   wherein the device is biodegradable.

2. The implant of claim 1, wherein said dopamine modulating compound is a dopamine agonist.

3. The implant of claim 2, wherein said dopamine agonist is apomorphine, lisuride, pergolide, bromocriptine, pramipexole, rotigotine, docarpamine, terguride, cabergoline, levodopa, spheramine, romergoline, carmoxirole, zelandopam, sumanirole, sibenadet, a 4-alkylamino-2(3H)-indolone compound or a combination thereof.

4. The implant of claim 3, wherein said 4-alkylamino-2 (3H)-indolone compound is of formula (I):

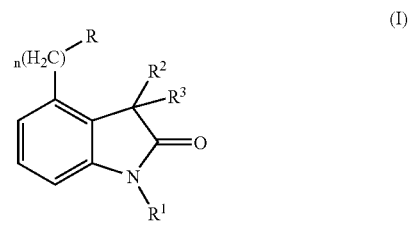

wherein:
   R is amino, alkylamino, di-alkylamino, alkenylamino, dialkenylamino, N-alkyl-N-alkenylamino, benzylamino, dibenzylamino, arylalkylamino, or diarylalkylamino; R1, R2 and R3 are each independently hydrogen or alkyl; and
   n is 1, 2, or 3, and pharmaceutically acceptable salts thereof.

5. The implant of claim 4, wherein said dopamine modulating compound is ropinirole.

6. The implant of claim 2, wherein said polymer comprises poly(glycolic acid), poly-D,L-lactic acid, poly-L-lactic acid, copolymers of the foregoing, poly(aliphatic carboxylic acids), copolyoxalates, polycaprolactone, polydioxonone, poly(ortho carbonates), poly(acetals), poly(lactic acid-caprolactone), polyorthoesters, poly(glycolic acid-caprolactone), polyanhydrides, natural polymers, or mixtures thereof.

7. The implant of claim 6, wherein said polymer is a polyglycolide/polylactide co polymer or polycaprolactone.

8. The implant of claim 2, wherein said dopamine modulating compound is present in an amount which is effective to treat a subject for a dopamine associated state.

9. The implant of claim 8, wherein said dopamine associated state is Parkinson's disease, attention deficit disorder (ADD), attention deficit hyperactivity disorder (ADHD), autism, pervasive development disorder (PDD), Asberger's syndrome, toxin-induced parkinsonism, disease-induced parkinsonism, erectile dysfunction, restless leg syndrome, or hyperprolactinemia.

10. The implant of claim 2, wherein said dopamine modulating compound is present in an amount which is effective to maintain a dopamine modulating compound level of between about 1 ng/ml and about 40 ng/ml in a subject for at least one day.

11. The implant of claim 10, wherein said dopamine modulating compound levels are maintained for at least one week.

12. The implant of claim 11, wherein said dopamine modulating compound levels are maintained for at least one month.

13. The implant of claim 12, wherein said dopamine modulating compound levels are maintained for at least three months.

14. The implant of claim 1, wherein said hydrophobic coating is PLA.

15. The implant of claim 6, wherein said polymer is PLA.

16. The implant of claim 2, wherein said implant is manufactured using a melt mix procedure.

* * * * *